United States Patent
Weadock et al.

(10) Patent No.: US 11,207,068 B2
(45) Date of Patent: Dec. 28, 2021

(54) ANVIL ASSEMBLY FOR USE WITH SURGICAL STAPLING INSTRUMENTS

(71) Applicant: Ethicon, Inc., Somerville, NJ (US)

(72) Inventors: Kevin Shaun Weadock, Hillsborough, NJ (US); Robert Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 259 days.

(21) Appl. No.: 15/802,660

(22) Filed: Nov. 3, 2017

(65) Prior Publication Data

US 2019/0133577 A1 May 9, 2019

(51) Int. Cl.
*A61B 17/072* (2006.01)
*A61B 17/115* (2006.01)

(52) U.S. Cl.
CPC ..... *A61B 17/07207* (2013.01); *A61B 17/1155* (2013.01); *A61B 2017/07228* (2013.01); *A61B 2017/07235* (2013.01); *A61B 2017/07242* (2013.01); *A61B 2017/07257* (2013.01); *A61B 2017/07264* (2013.01)

(58) Field of Classification Search
CPC .......... A61B 17/07207; A61B 17/1155; A61B 2017/07228; A61B 2017/07235; A61B 2017/07242; A61B 2017/07257; A61B 2017/07264
USPC ........................................... 227/175.1–182.1
See application file for complete search history.

(56) References Cited

U.S. PATENT DOCUMENTS

| | | | |
|---|---|---|---|
| 4,767,044 A | 8/1988 | Green | |
| 6,978,922 B2 | 12/2005 | Bilotti et al. | |
| 8,613,384 B2 * | 12/2013 | Pastorelli | A61B 17/072 227/177.1 |
| 10,314,582 B2 * | 6/2019 | Shelton, IV | A61B 17/068 |
| 2007/0194082 A1 | 8/2007 | Morgan et al. | |
| 2007/0262116 A1 * | 11/2007 | Hueil | B25C 5/0292 227/175.1 |
| 2014/0103092 A1 | 4/2014 | Kostrzewski et al. | |
| 2015/0297236 A1 * | 10/2015 | Harris | A61B 17/1155 227/176.1 |
| 2016/0089147 A1 * | 3/2016 | Harris | A61B 17/0684 227/176.1 |
| 2016/0270792 A1 * | 9/2016 | Sniffin | A61B 17/07207 |
| 2016/0287249 A1 * | 10/2016 | Alexander, III | A61B 17/0644 |
| 2017/0196564 A1 * | 7/2017 | Sgroi | A61B 17/07207 |
| 2018/0168584 A1 * | 6/2018 | Harris | A61B 17/07207 |
| 2019/0046190 A1 * | 2/2019 | Dunki-Jacobs | A61B 17/072 |

FOREIGN PATENT DOCUMENTS

| | | |
|---|---|---|
| DE | 2109604 | 9/1971 |
| EP | 338651 | 10/1989 |
| EP | 2425788 | 3/2012 |

(Continued)

*Primary Examiner* — Anna K Kinsaul
*Assistant Examiner* — Himchan Song
(74) *Attorney, Agent, or Firm* — David R. Crichton; Leo Kriksunov

(57) ABSTRACT

A surgical stapler having an anvil including a plurality of staple forming pockets for forming staples. The staple forming pockets include first and second staple forming cups configured to receive first and second legs of a staple respectively. The first staple forming cup within each staple forming pocket has a different depth from the second staple forming cup within that staple forming pocket.

14 Claims, 10 Drawing Sheets

(56) References Cited

FOREIGN PATENT DOCUMENTS

| EP | 3348208 | 7/2018 |
|----|---------|--------|
| GB | 1299336 | 12/1972 |
| WO | WO 2016048648 | 3/2016 |

* cited by examiner

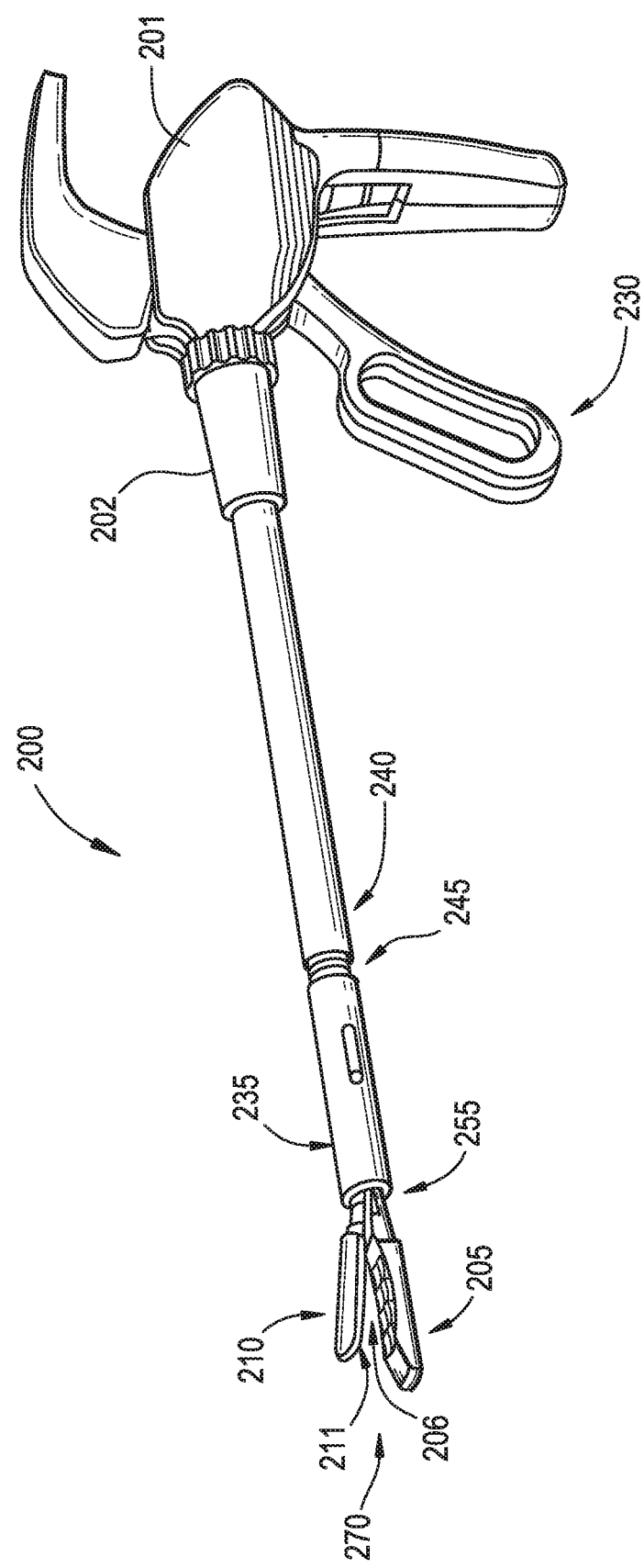

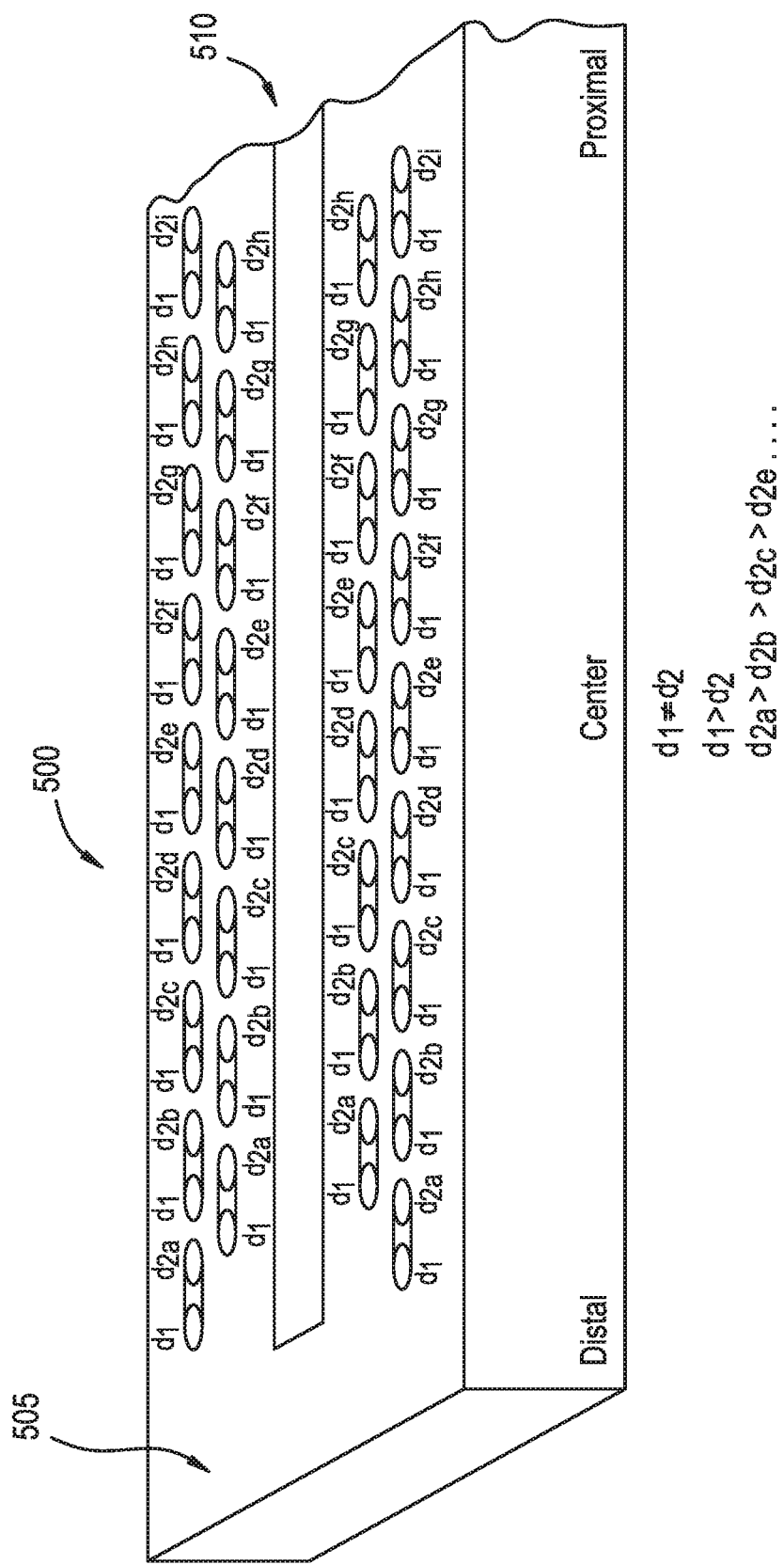

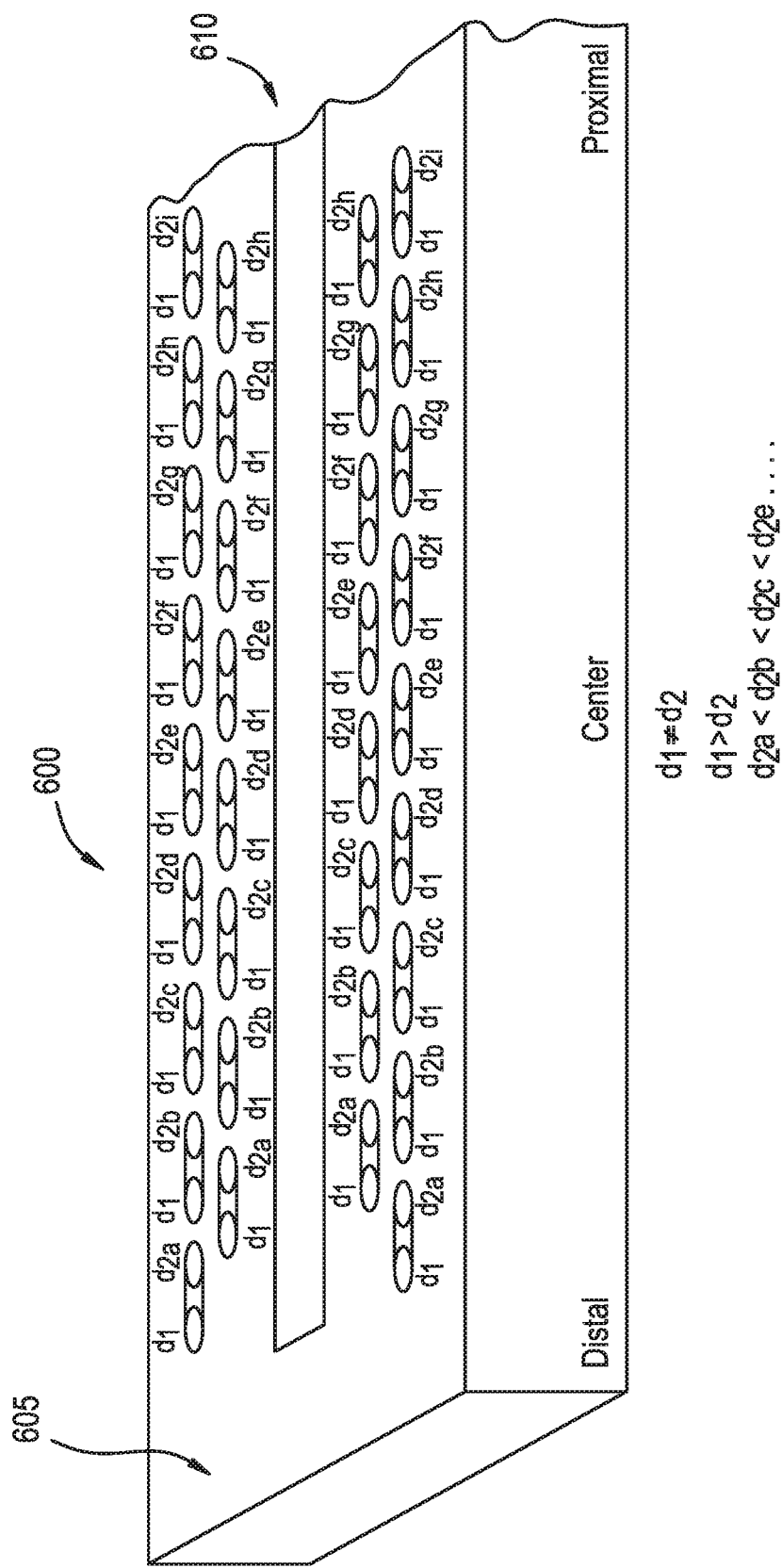

ANVIL ASSEMBLY FOR USE WITH SURGICAL STAPLING INSTRUMENTS

FIELD OF THE INVENTION

The field of art to which this invention pertains is medical devices and methods for stapling tissues together, relating to staplers for preventing leaks in tissues having varying thickness along the staple line. This invention more particularly relates to surgical staplers having anvils with staple forming pockets and staple forming cups for forming staples.

BACKGROUND OF THE INVENTION

Surgical stapling instruments have become critical to many lifesaving surgical procedures. Surgical staples are usually mechanically inserted into tissue with surgical stapling instruments, such as those known as anastomosis devices, including gastrointestinal anastomosis devices and transverse anastomosis devices. The staples typically are made from stainless steel or titanium. The un-deformed staple is generally U-shaped and includes a back span and two legs extending substantially perpendicularly from the back span. Each leg has a sharp chiseled end point for piercing body organs or tissue. In such devices, the staples are loaded in one or more elongated rows into a cartridge. A mechanism for pushing, or driving the stapler is actuated to drive the staples through two or more sections of tissue toward an anvil. The anvil includes a plurality of staple pockets formed in the surface of the anvil, with each staple pocket including first and second staple forming cups. The pockets and staple forming cups deform staples into a substantially B-shaped configuration, with the B-shape staple being the gold standard for staple formation, in that it is believed this configuration provides a lower chance of leak from the staple line. Gastrointestinal anastomosis-type devices drive and bend the staples aligned in a row sequentially in rapid sequence, while transverse anastomosis-type devices drive and bend all staples simultaneously. Circular anastomosis-type devices simultaneously apply annular rows of staples to tissue.

FIG. 1 illustrates regions of the human stomach that are of interest to surgeons when performing a sleeve gastrectomy. The line of proposed stapling is dashed. In both males and females, the stomach is thickest near the pyloric antrum and thinnest near the fundus. For females, typical thickness measurements of the antrum are approximately 2.0-4.5 mm, the mid-body 1.5-4.0 mm, and fundus 1.0-3.7 mm. For males, typical thickness measurements of the antrum are approximately 2.5-5.7 mm, the mid-body 1.5-3.5 mm, and fundus 1.5-2.5 mm. In order to accommodate various tissue thicknesses, surgeons have a choice of staple lengths that may be suitable. The choice of the appropriate staple length is critical to ensuring that a sound apposition is produced as a result of the stapling process. Unfortunately, the surgeon must estimate tissue thickness and attempt to select the appropriate length staple that they think will provide an adequate apposition of the tissues. The choice of a staple for a given tissue may also depend on the disease state. For example, in emphysematous lung tissue, which has been thinned out, a short staple is needed. For pulmonary fibrosis, a taller staple is needed. Thus, using staples that are too small or too large can compromise staple line integrity. Staples that are too small may form too tightly and potentially compress the tissue causing local ischemia or may be too small to form the necessary closed form and thereby create a potential leak. Staples that are too large may fully form without actually achieving the necessary compression of tissue to seal the wound and thereby create a point of leakage. Open staple heights can vary from 2.0 mm to 4.4 mm and closed staple heights can vary from 0.75 mm to 2.3 mm. Table 1 below illustrates the tissue thicknesses that are commonly stapled and the variations in staple heights in the open and closed position. The cartridges are typically color coded to enable the surgeon to select the desired staple height.

TABLE 1

| Cartridge Color | Tissue/Thickness | Open Staple Height | Closed Staple Height |
| --- | --- | --- | --- |
| Purple | Mesentery/Thin | 2.0 mm | 0.75 mm |
| Blue | Regular | 3.5 mm | 1.5 mm |
| Gold | Regular/Thick | 3.8 mm | 1.8 mm |
| Green | Thick | 4.1 mm | 2.0 mm |
| White | Vascular/Thin | 2.5 mm | 1.0 mm |
| Black | Very Thick | 4.4 mm | 2.3 mm |

In clinical practice, a surgeon may use only one type of staple cartridge to create the entire sleeve. However, this method risks bleeding or leaking if the thickness of the stomach is outside the indicated range of the cartridge. In an alternative method, the surgeon starts with the thickest load (the black cartridge) and then chooses subsequent staple loads based on how the tissues feel. The downfall of this tactile-feedback method is its subjectivity. Without an objective measurement, an incorrect staple height may be chosen and lead to incomplete staple formation, leakage, or bleeding.

In US patent application 2014-0103092, a triple staple configuration is disclosed and attempts to address the problem of leaking from stapled tissues by offering a stapler that applies parallel rows of staples, with a total of three different staple heights per cartridge as well as a varying height of the tissue contacting surfaces. The stapler is configured to deliver multiple rows of staples, with each row parallel to the longitudinal axis of the device, and each row is configured with only one length of staple. The abutting rows are configured with staples of a different length. The tissue contacting surfaces are produced as a series of surfaces that run parallel with the rows of staples and each surface is at a different height than the abutting parallel surface. This configuration of stapler provides multiple full parallel rows of staples formed at distinct heights. While each row of staples may be of a different height, any full row of staples is only formed to one height. The gap between the anvil and the driver sides of the jaw is limited to what is possible with the compression of the thickest tissue within the jaw coupled with the narrowest gap formed between the tissue contacting surfaces. The potential compression distance of each staple leg in any given row is the same per individual staple. This stapler design would inadequately address any potential rapid change in tissue thickness along the axis of the tissue to be stapled, i.e. offset locations parallel to the centerline of the jaw of the instrument as the clamping of the narrowest tissue contacting surfaces with the thick condition of the clamped tissue maintains the jaws too far apart to enable full staple formation. In US 2007-0194082 designs employing anvils that have two populations of staple pockets, with full line abutting staple pocket depths in one population having depths greater than depths of the abutting full line of staple pockets in the other population. Other strategies to adjust for tissue thickness have been disclosed in U.S. Pat. Nos. 6,978,922 and 4,767,044. Neither of these designs enable the surgeon to safely staple tissues having rapidly changing changes in tissue thickness. What is needed is a stapling device that enables every staple to address variability in tissue thickness that provides a broader range of thickness coverage from one size staple that is deformed than traditional uniformly deformed staples. Such a stapler would enable the surgeon to reduce the incidence of leakage along the staple line.

SUMMARY OF THE INVENTION

The present application discloses an anvil assembly for use with a surgical stapler that includes staple forming pockets configured to receive first and second staple legs of a staple. Each of the staple forming pockets has a first staple forming cup with a first depth and second staple forming cup with a second depth, wherein the first depth is different than the second depth. The plurality of staple forming pockets may be aligned in first and at least a second spaced apart rows. They may be aligned as linear rows or annular rows.

In one embodiment, the depth of a staple forming cup in a staple forming pocket on a first row has a different depth than the closest staple forming cup on the second row. In another embodiment, for each of the first and second rows, the first depth of all staple forming cups said row is equal and the second depth of all staple forming cups in said row is variable. The first and second staple forming cups may further be aligned at an angle with respect to an axis of the row.

Also provided is a surgical stapler having a staple cartridge having a plurality of directionally aligned staples contained therein and pushers to advance the staples, and an anvil assembly. The anvil assembly includes a tissue contact surface having a plurality of staple forming pockets formed therein. Each of the plurality of staple forming pockets includes first and second staple forming cups, where each of the staple forming cups has a depth, and where for each staple forming pocket, the first staple cup has a depth that is greater than the second staple forming cup.

The staple forming pockets may be aligned as a first row and at least a second row. In one embodiment, the depth of a staple forming cup in a staple forming pocket on the first row has a different depth than the closest staple forming cup on the second row.

The first and second rows may be aligned as linear rows or as annular rows. In one embodiment, the first depth of all staple forming cups on a first row is equal to one another and the second depth of all staple forming cups in the first row is of variable depth. In another embodiment, the first and second staple forming cups are aligned at an angle with respect to the axis of the row of staple forming cups.

These and other aspects and advantages of the present invention will become more apparent from the following description and accompanying drawings.

BRIEF DESCRIPTION OF THE DRAWINGS

FIG. 2 illustrates an exemplary surgical stapler that may incorporate teachings of the present disclosure;

FIG. 5 illustrates a perspective view of alternate embodiment of an anvil assembly of a linear stapler having staple forming pockets with a first staple forming cup of fixed depth and a second staple forming cup depth that decreases from the distal end to the proximal end of the anvil;

FIG. 6 illustrates a perspective view of alternate embodiment of an anvil assembly of a linear stapler having linear rows of staple forming pockets with a first staple forming cup of fixed depth and a second staple forming cup depth that increases from the distal end to the proximal end of the anvil;

DETAILED DESCRIPTION OF THE INVENTION

Figure 1:
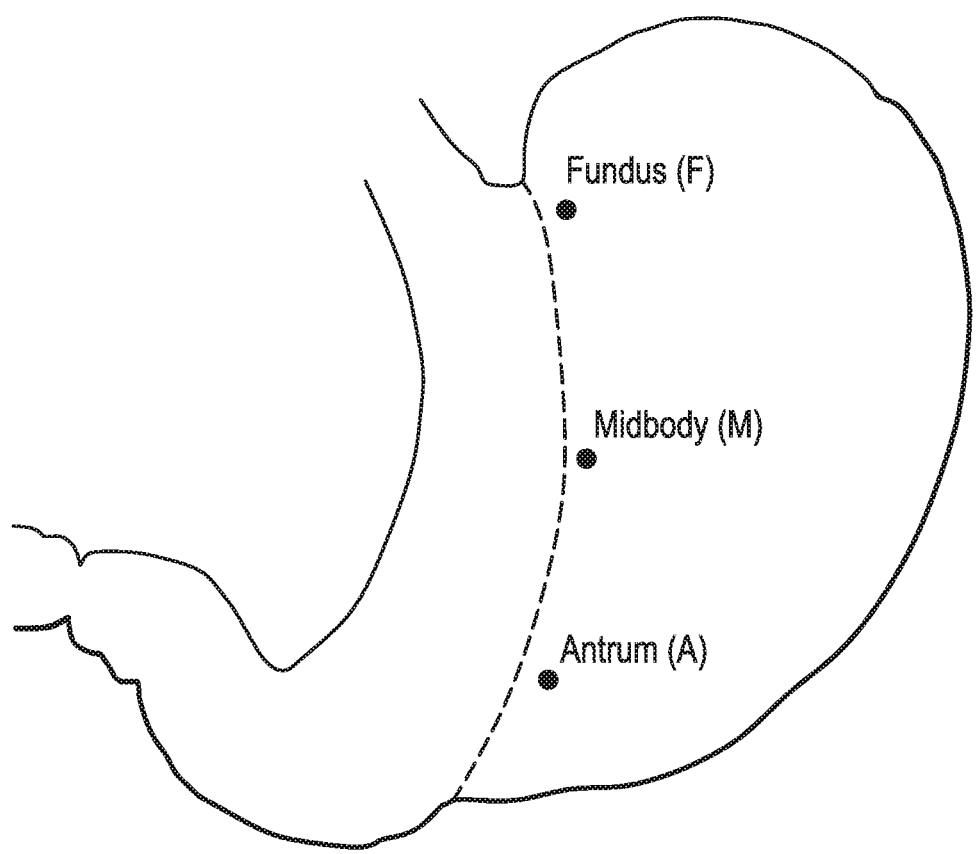
FIG. 1 illustrates the human stomach anatomy.

In one aspect, the present disclosure describes an anvil assembly for use with surgical staplers, which include but are not limited to endocutters, circular staplers, curved cutter staplers, linear cutters and staplers, and hemorrhoidal staplers. The anvil assembly has a tissue contact surface that includes at least one staple pocket, and typically a plurality of staple pockets, having first and second staple forming cups. The first and second staple forming cups are configured to receive first and second legs of a staple, and each has a different depth. The varying staple forming cup depths enable the stapler to account for variations in tissue thickness that may occur parallel to and within at least one of the proposed staple lines. This is important as it reduces the likelihood of leakage across the staple line.

FIG. 2 illustrates an exemplary linear surgical stapler 200 that can incorporate an anvil assembly as described herein. Those skilled in the art will readily understand that the present invention is not limited to the stapler illustrated in FIG. 2, but rather the principles described herein can be incorporated into any suitable surgical stapler. The stapler 200 includes a handle 201 with a pivotable trigger 230, an elongate hollow shaft 240 extending from the handle between a proximal end 202 and a distal end 235. Positioned at the distal end of the shaft is a staple cartridge assembly 205 and opposed anvil assembly 210. The cartridge assembly 205 is pivotable about pivot point 255, and the elongate shaft may also include a pivot point 245 to improve movement and positioning of the instrument for optimal stapling. The staple cartridge assembly 205 and the opposed anvil assembly 210 have tissue contacting surfaces 206 and 211, respectively, and apertures in the staple cartridge assembly 205 are aligned with staple forming pockets in the anvil assembly 210 as will be described in further detail below. The pivotable trigger 230 is actuable through an actuation stroke or strokes to move the anvil assembly 210 in relation to the cartridge assembly 205 between an open position and a clamped position and to eject staples from the cartridge assembly 205. Alternatively, the actuation stroke may pivot the cartridge assembly 205 towards the anvil assembly 210 such that the staples may be formed against staple forming pockets.

Figure 3A:
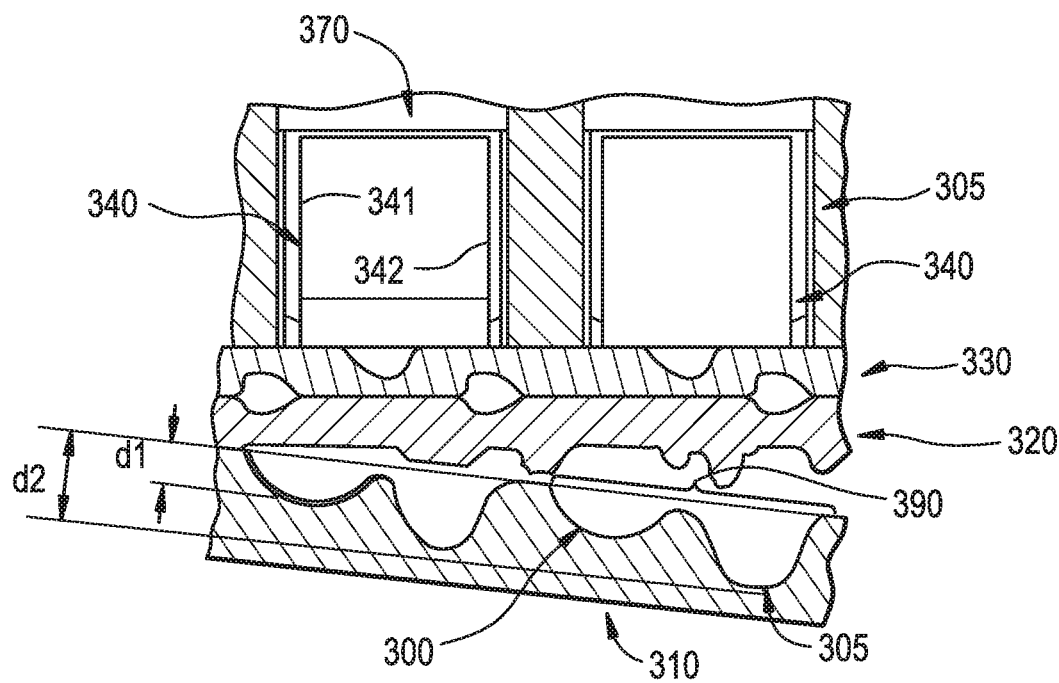
FIG. 3A illustrates an enlarged cross-sectional view of one embodiment of a staple cartridge according to the present disclosure.
Figure 3B:
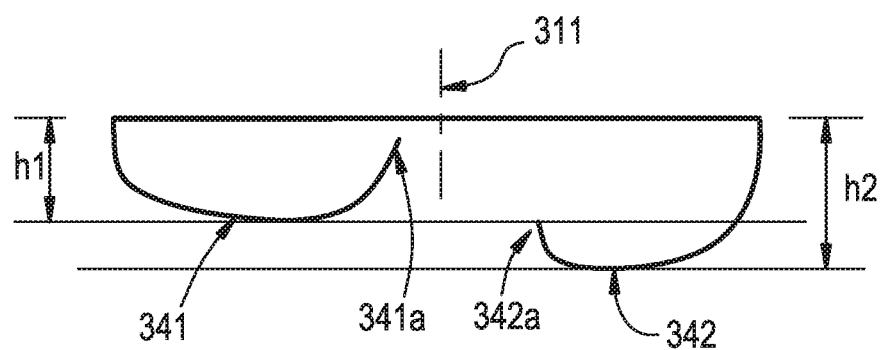
FIG. 3B illustrates an exemplary staple formed using a surgical stapler as described herein.

FIG. 3A illustrates an enlarged view of one embodiment of a staple cartridge 305 and anvil assembly 310 according to the present disclosure that can be incorporated into a surgical stapler such as the one illustrated in FIG. 2. FIG. 3A illustrates two staples 340 within the staple cartridge 305 just prior to firing the staples through two layers of tissue 320 and 330. For each staple 340 there is a corresponding staple pocket 390 on the anvil 310. Each staple pocket 390 has two staple forming cups 300, 305 that each receive a respective single staple leg 341, 342 during the stapling process. Staple forming cup 300 has a depth $d_1$ that is less than the depth $d_2$ of staple forming cup 305, such that comparatively speaking, staple forming cup 305 is deeper and staple forming cup 300 is more shallow in depth. Thus, after stapling, there will be two different closed staple heights per staple as illustrated in FIG. 3B. Both legs 341, 342 start off with the same length prior to stapling, but the first staple leg 341 that goes into staple forming cup 310 which has a more shallow depth $d_1$ will have a smaller height of approximately $h_1$ and its tip 341a will come closer to the middle of the arch 311 of the staple. The staple leg 342 that gets pushed into staple forming cup 305 which has a deeper depth $d_2$ will have a greater height of approximately $h_2$ but the tip 342a will not come as close to the middle of the arch 311 of the staple.

Figure 4A:
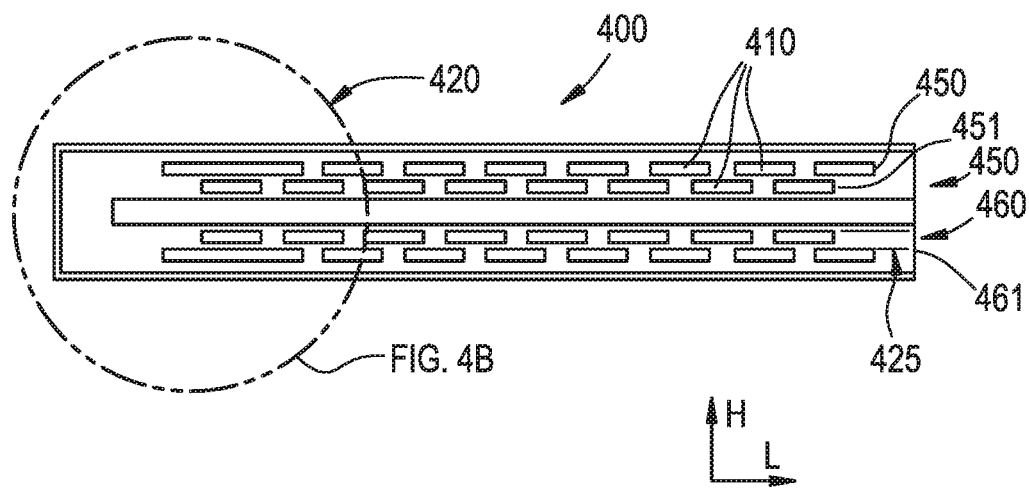
FIG. 4A illustrates one embodiment of an anvil assembly of a linear stapler having staple forming pockets with staple forming cups of different depth.
Figure 4B:
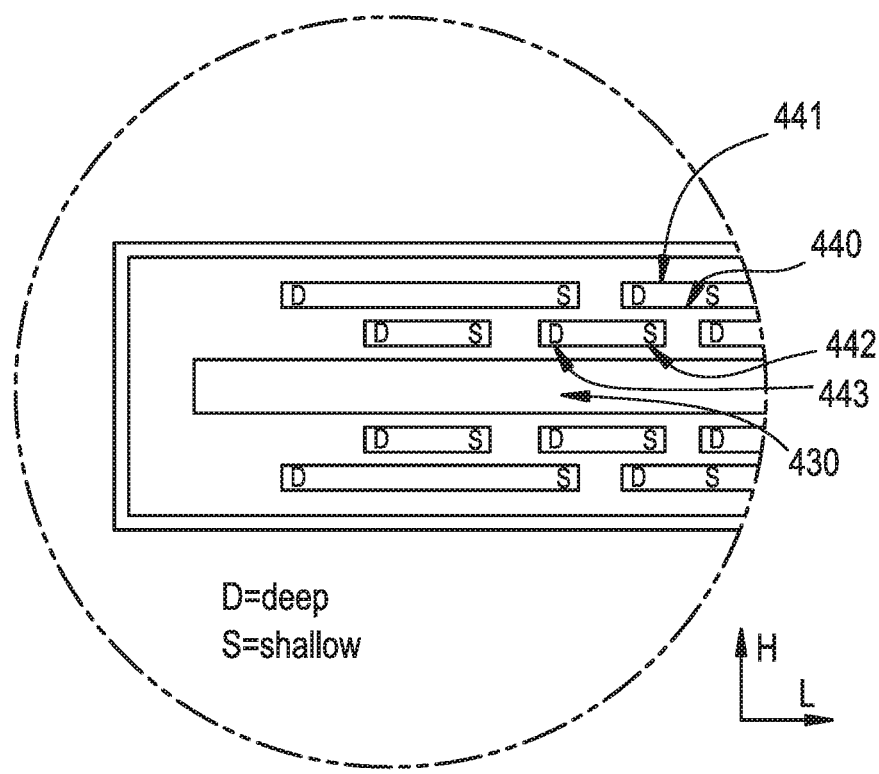
FIG. 4B is an enlarged view; of the circled portion of the anvil assembly of FIG. 4A.

FIGS. 4A-4B illustrates the tissue contacting surface 425 of an exemplary anvil assembly or anvil 400. For purposes of clarity, the terms anvil assembly and anvil will be used interchangeably. The tissue contacting surface 425 includes a series of staple forming pockets 410 that are aligned with staple apertures in the tissue contacting surface of the staple cartridge (not shown) as described above. The staple cartridge houses staples that are supported by pushers within the staple apertures of the cartridge (not shown). The pushers will be used to drive the staples against the staple forming pockets 410 of the anvil assembly 400 in any well-known manner when the cartridge is actuated. The tissue contact surface of the staple cartridge also includes a slot 430 for a knife (not shown) to cut through tissue after the stapling process is completed. An enlarged view of one end 420 of the anvil 400 illustrates how each staple forming pocket 410 has first and second staple forming cups 440 and 441. In the illustrated embodiment, on each side of the slot 430 are two rows 450, 451 and 460, 461 of staple forming pockets, with the two rows on each respective side of the slot being staggered with respect to one another. As a result, a staple forming pocket on the rows of staple forming cups closest to the slot 430 may have a deeper (D) staple forming cup 440 while the adjacent staple forming cup 440 in the row of staple forming cups furthest from the slot 430 has a more shallow (S) cup next to it. This configuration allows for the stapler to compensate for tissue thickness variations, since a single staple forming cup 441 that is deeper staple forming cup will capture thicker tissue while the more shallow staple forming cup 440 will capture thinner tissue. Since there is alternation of deeper staple forming cups (D) and more shallow staple forming cups (S) in both the linear (L) and horizontal (H) directions, the anvil reduces the probability that a sudden change in tissue thickness will result in inadequate stapling and possible leaks along the staple line. To address the concern that a single closed staple length may be too short to close a section of tissue that is thicker than the closed staple height, the rows of staple forming pockets 450, 451 and 460, 462 may be staggered with respect to one another. In one embodiment, however, the rows are not staggered with respect to one another. In either case, if a given closed staple height is too short for the tissue thickness, the adjacent staple on the adjacent row of staples will have the taller closed staple height. Various combinations of staple forming cup depths can be used to achieve optimal stapling of tissue having variable thickness.

In one embodiment illustrated in FIG. 5, a row of staple forming pockets on an anvil 500 is comprised of a series of staple forming pockets, each staple forming pocket having a first staple forming cup of a first depth $d_1$ and a second staple forming cup of a second depth $d_2$, the second staple cup depth $d_2$ being different than the first staple forming cup $d_1$ depth. As illustrated, the second staple cup depth $d_2$ is less than the first staple forming cup $d_1$, with the depth of staple forming cup $d_2$ gradually decreasing from the distal end 505 of the row of staple forming pockets to the proximal end 510, i.e., $d_{2a} > d_{2b} > d_{2c}$. A gradient of staple forming cup depths exists for only d2, while d1 remains constant along the length of the anvil. In another embodiment illustrated in FIG. 6, $d_1$ is fixed for all staple forming cups along the row of staple forming pockets on the anvil 600 while $d_2$ gradually increases in depth from the distal end 605 of the anvil 600 to the proximal end 610 of the anvil. In yet another embodiment, $d_1$ is fixed for all staple forming pockets along the row of staple forming pockets while $d_2$ gradually increases from the proximal end of the anvil to the center of the anvil and then decreases to the distal end of the anvil. In yet another embodiment, $d_1$ is fixed for all staple forming pockets along the row of staple forming pockets while $d_2$ gradually decreases from the proximal end of the anvil to the center of the anvil and then increases to the distal end of the anvil.

Figure 7:
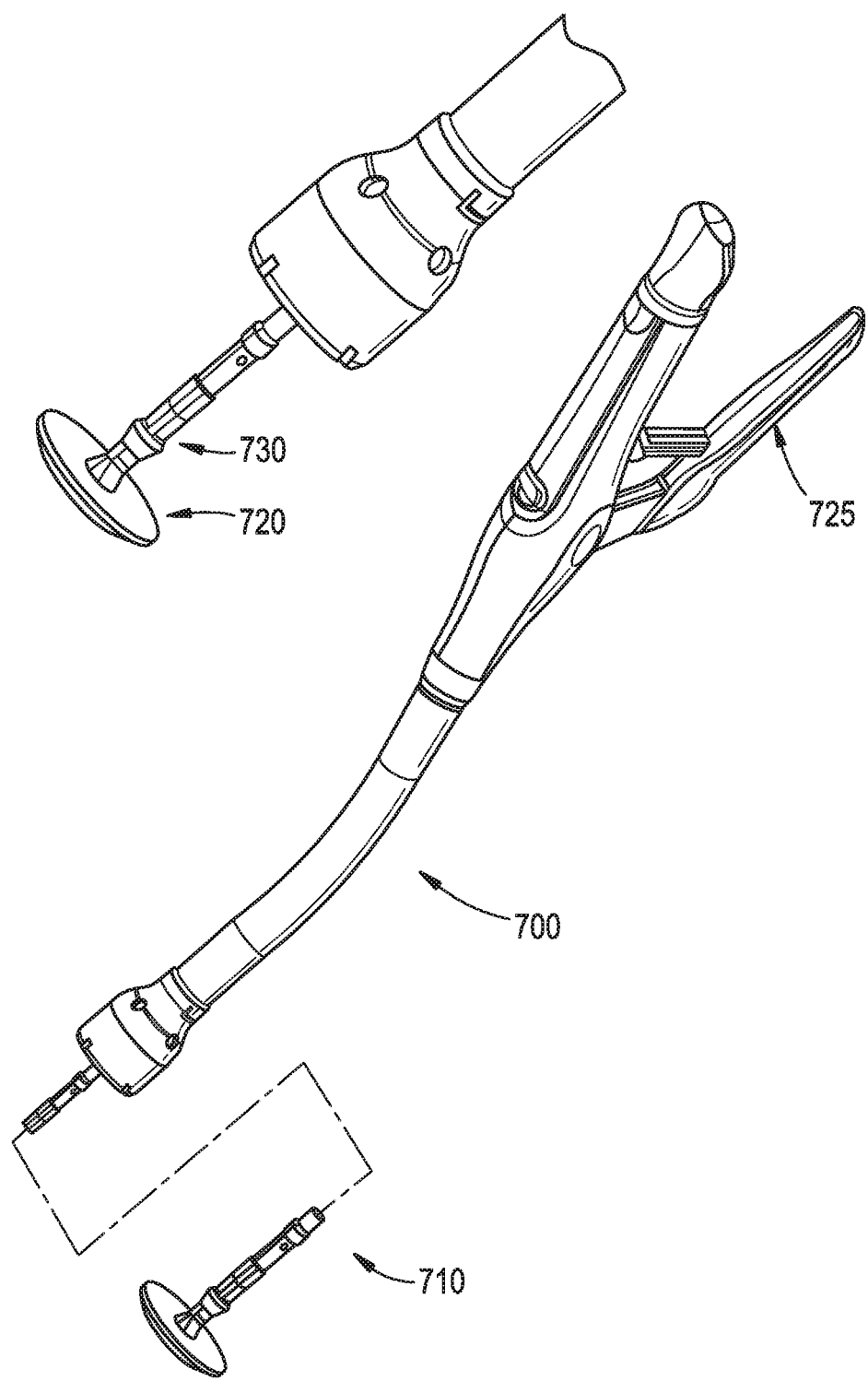
FIG. 7 illustrates an exemplary circular stapler that may incorporate teachings of the present disclosure.
Figure 8A:
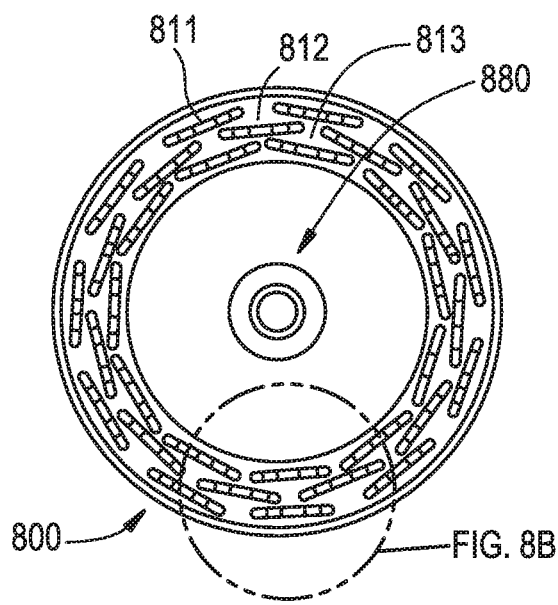
FIG. 8A illustrates one embodiment of an anvil assembly of a circular stapler having annular rows of staple forming pockets, with a first staple forming cup of fixed depth and a second staple forming cup depth that decreases from the inner row to the outer row.
Figure 8B:
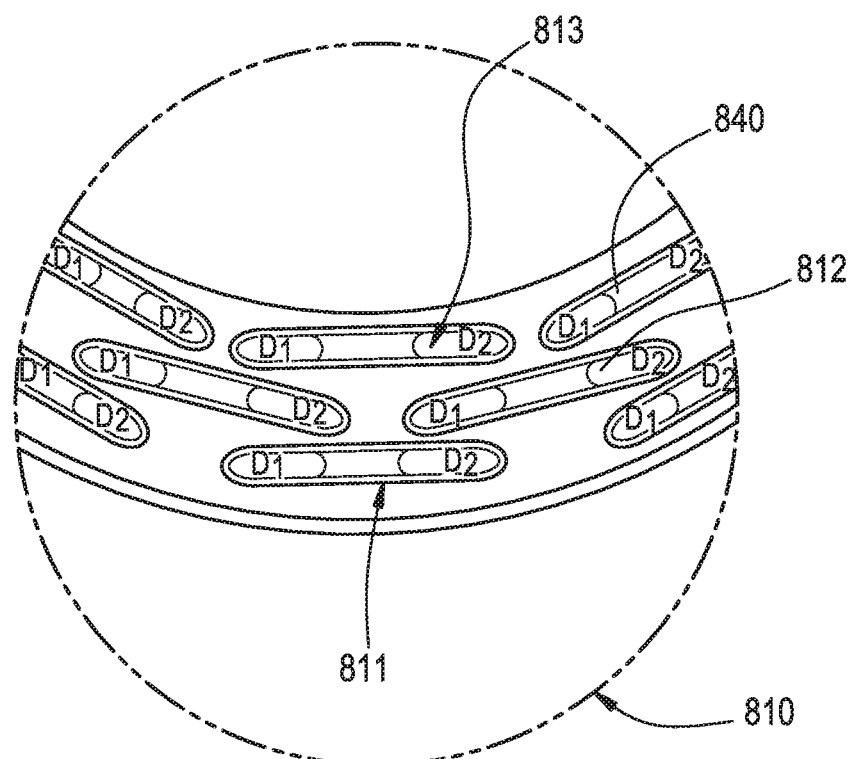
FIG. 8B is an enlarged view of the circled portion of the anvil assembly of FIG. 8A.

An anvil according to the present disclosure can also be incorporated into a circular stapler 700 as shown in FIG. 7. Circular staplers are most commonly used to create an anastomosis between two segments of the bowel. The stapler has a shaft 730 that is coupled to a removable anvil 710 which has a tissue facing surface 720. FIGS. 8A-8B illustrates in greater detail the tissue facing surface of the anvil assembly, with an enlarged view shown in circle 810. The exemplary anvil has three annular rows 811, 812, and 813 of staple forming pockets, with each staple forming pocket having two staple forming cups of depths $d_1$ and $d_2$, with $d_1$ having a different depth than $d_2$ in a manner analogous to that described in conjunction with the exemplary linear staplers. The center of the anvil 880 is connected to the shaft. In one embodiment, the inner row 813 of staple forming pockets have staple forming cups depth $d_1$ and $d_2$, respectively and where $d_1$ is greater than $d_2$. The middle row 812 of staple forming pockets also has staple forming cups with depths $d_1$ and $d_3$, where $d_3$ is less than $d_2$ on the inner row. The outer row 811 of staple forming pockets has staple forming cups with depths $d_1$ and $d_4$, respectively and where $d_4$ is less than $d_3$ on the middle row. In all the annular rows of staple forming pockets, each staple forming pocket has a first staple forming cup of a depth $d_1$ but the other rows have a different depth for the second staple forming cup.

Figure 9A:
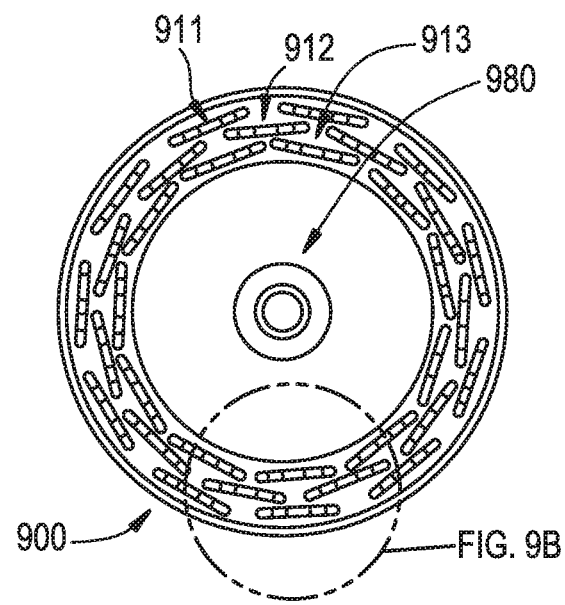
FIG. 9A illustrates an alternate embodiment of an anvil assembly of a circular stapler having rows of staple forming pockets and staple forming cups of different depths.
Figure 9B:
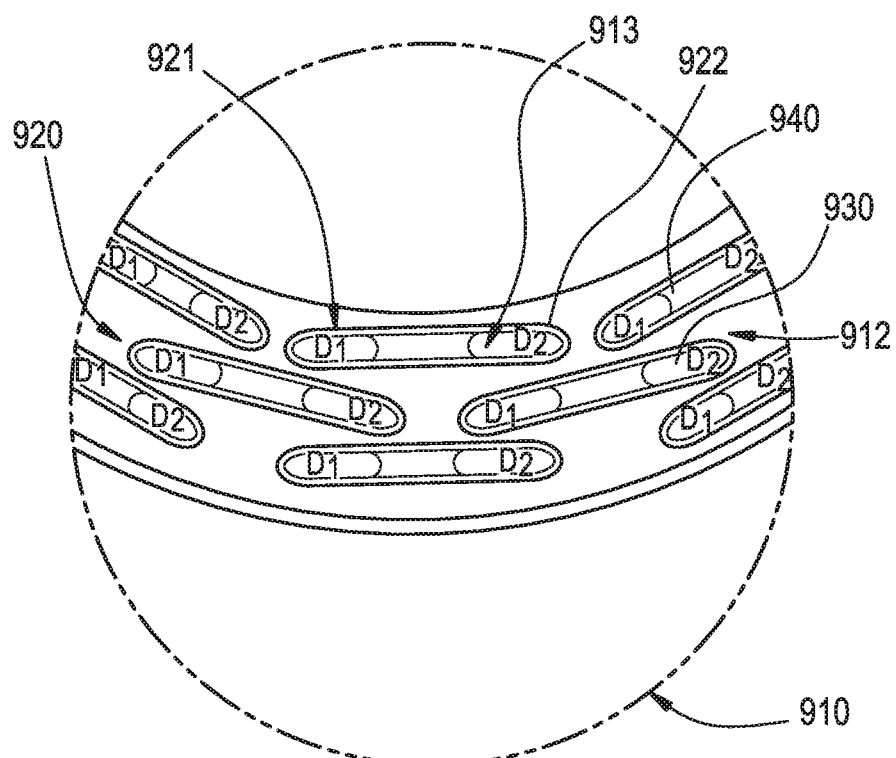
FIG. 9B is an enlarged view of the circled portion of the anvil assembly of FIG. 9A.

In another embodiment illustrated in FIGS. 9A-9B, the anvil assembly similarly has three annular rows 911, 912, and 913 of staple forming pockets. In one embodiment, the inner row 913 of staple forming pockets have staple forming cups 921 and 922 with deeper (D) and more shallow (S) depths, respectively. The outer row 911 has a staple forming pocket 940 having a first staple forming cup of a first depth and a second staple forming cup of a second depth, wherein the first depth is different than the second depth. Adjacent to staple forming pocket 940 are two other staple forming pockets 920 and 930. In this embodiment, the pockets are arranged so that the more shallow staple forming cup of one pocket (i.e., 940) is adjacent to the deeper staple forming cup of another staple forming pocket (i.e., 920 and 930). This configuration allows for the stapler to compensate for tissue thickness variations, since a staple forming pocket with a deeper staple forming cup will be aligned adjacent to a staple forming pocket with a more shallow staple forming cup.

Figure 10A:
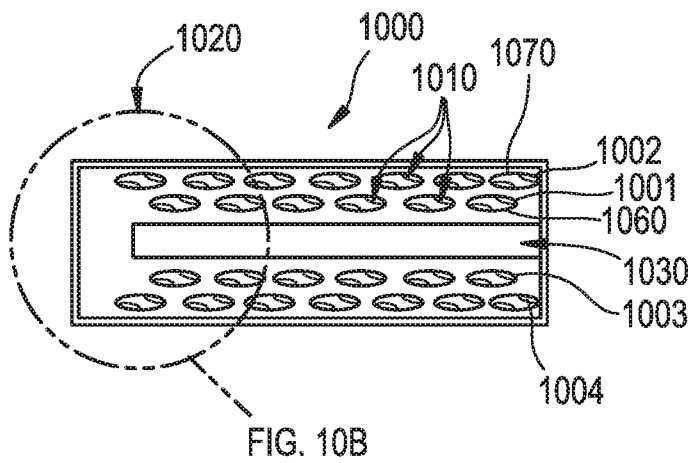
FIG. 10A is an alternate embodiment of a linear anvil having staple forming cups formed at an angle with respect to the axis of the row of staple forming pockets.
Figure 10B:
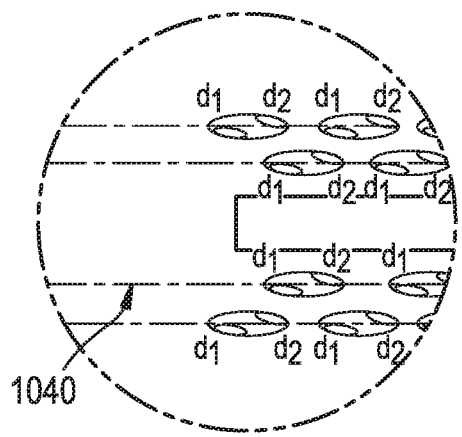
FIG. 10B is an enlarged view of a portion of the anvil assembly of FIG. 10A
Figure 10C:
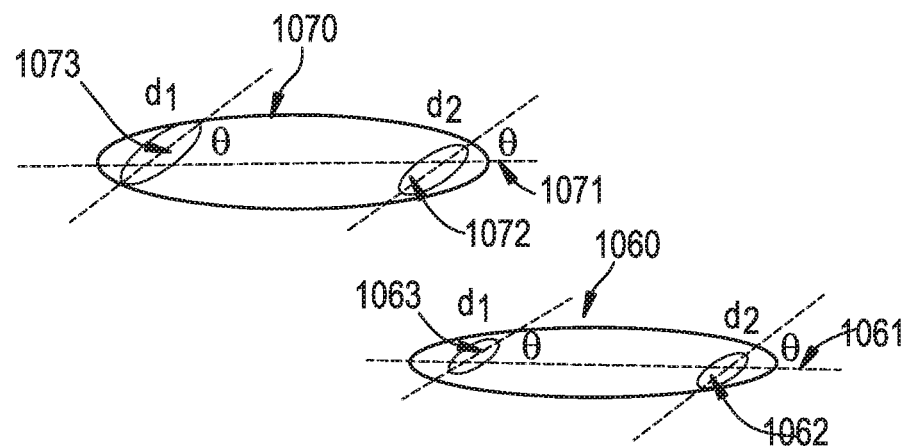
FIG. 10C illustrates representative staple forming cups of FIGS. 10A and 10B.
Figure 10D:
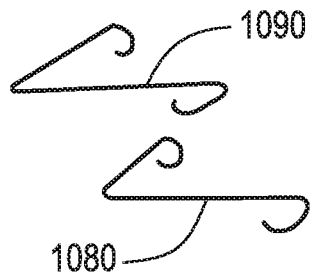
FIG. 10D illustrates a staple formed using the device of FIGS. 10A-10C.

In all embodiments of the anvil described herein, staple cup depth can range from 0.5 mm-3.0 mm. In one embodiment, the more shallow staple cup depths on a particular staple forming pocket is 1.25 mm and the deeper staple forming cup is 2.1 mm. The difference in staple cup depths within a single staple forming pocket may vary from 0.25 to 2.0 mm. In one embodiment, a staple forming pocket has a first staple forming cup of depth $d_1$ and a second staple forming cup with depth $d_2$, and the difference in depth between $d_1$ and $d_2$ is 0.5 mm. In one embodiment, a staple forming pocket has a first staple forming cup of depth $d_1$ and a second staple forming cup with depth $d_2$, and the difference in depth between $d_1$ and $d_2$ is 2.0 mm. In one embodiment illustrated in FIGS. 10A-10C, the staple forming cups $d_1$ and $d_2$ within any staple forming pocket 1010 on the anvil 1000 can be parallel to one another but at an angle with respect to the axis 1040 of the row of staple forming pockets. A slot 1030 for a blade (not shown) to cut tissue is shown on the tissue contacting surface of the anvil 1000 as are first and second parallel but spaced apart rows of staple forming pockets on opposite sides of the slot 1001, 1002 and 1003, 1004. FIG. 10C illustrates how a first staple forming cup 1072 in a first staple forming pocket 1070 on second row 1002 would enable a staple leg to be bent to a depth $d_2$ away from the axis 1071 and towards the staple leg of a staple formed in a staple forming cup 1063 with depth $d_1$ on a first row 1002 aligned on axis 1061. The staple forming cups 1062 and 1063 are all angled away from the axis 1061 of the staple forming pocket. In corresponding fashion, the staple forming cups 1072 and 1073 are all angled away from the axis 1071 of the staple forming pocket. The angle θ can range from 3-45 degrees. In one embodiment, the angle θ formed is 5 degrees. In one embodiment, the angle θ formed is 30 degrees. In this anvil configuration, three dimensional staples as illustrated in FIG. 10D can be formed, with one leg of the staple being bent in the opposite direction of the other staple leg and with one staple leg being bent to a different closed staple height than the other staple leg on the same staple. Thus, a staple leg of a first staple 1090 that was bent in a short staple cup depth $d_1$ being near a staple leg of a second staple 1080 that was bent in a deep staple forming cup with depth $d_2$ from an adjacent row of staple forming pockets. Materials used to form the anvil can be selected from the group consisting of metal, ceramic, plastic, polymer, and glass. In one embodiment, the anvil is made from 400-series stainless steel.

Although specific embodiments of the present disclosure have been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present disclosure which is defined in the following claims, the scope of which is to be accorded the broadest interpretation so as to encompass such modifications and equivalent structures.

We claim:

1. An anvil assembly for use with a surgical stapler, said anvil assembly comprising:
   a planar tissue contacting surface;
   a plurality of staple forming pockets having an inner surface extending into the anvil assembly from the planar tissue contacting surface wherein each of said staple forming pockets is configured to receive first and second staple legs of a staple, and each of the staple forming pockets having a first staple forming cup further extending into the staple forming pocket from the inner surface, and thus further into the anvil assembly, from the planar tissue contacting surface with a first depth, as measured orthogonal to the planar tissue contacting surface from which the first depth extends, and a second staple forming cup further extending into the staple forming pocket from the inner surface, and thus further into the anvil assembly, from the planar tissue contacting surface with a second depth, as measured orthogonal to the planar tissue contacting surface from which the second depth extends, wherein the first depth is different than the second depth.

2. The anvil assembly of claim 1, wherein the plurality of staple forming pockets are aligned in a first row and at least a second row spaced apart from the first row.

3. The anvil assembly of claim 2, wherein the depth of any one of the staple forming cups in any one of the staple forming pockets on the first row has a different depth than the closest staple forming cup in a staple forming pocket on the second row.

4. The anvil assembly of claim 2, wherein the first and second rows are aligned as linear and parallel rows.

5. The anvil assembly of claim 2, wherein the first and second rows are aligned as annular rows.

6. The anvil assembly of claim 2, wherein for each of the first and second rows, the first depth of all staple forming cups in either the first or the second row is uniform and the second depth of all staple forming cups in either the first or the second row is variable.

7. The anvil assembly of claim 4, wherein the first and second staple forming cups are aligned at an angle with respect to an axis of the row.

8. A surgical stapler comprising:
   a staple cartridge having a plurality of directionally aligned staples contained therein and pushers to advance the staples; and
   an anvil assembly comprising a tissue contact surface and a plurality of staple forming pockets having an inner surface formed in the tissue contact surface, wherein each of said staple forming pockets is configured to receive first and second staple legs of a staple, and wherein each of the plurality of staple forming pockets includes first and second staple forming cups further extending into the staple forming pocket from the inner surface, and thus further into the anvil assembly, each of the staple forming cups having a depth, as measured orthogonal to the tissue contact surface from which the depth extends, and wherein for each staple forming pocket, the depth of the first staple cup is greater than the depth of the second staple forming cup.

9. The surgical stapler of claim 8, wherein the plurality of staple forming pockets are aligned as a first row of staple forming pockets and at least a second row of staple forming pockets.

10. The surgical stapler of claim 9, wherein the depth of a staple forming cup in a staple forming pocket on the first row has a different depth than the closest staple forming cup on the second row.

11. The surgical stapler of claim 9, wherein the first and second rows are aligned as linear rows.

12. The surgical stapler of claim 9, wherein the first and second rows of staple forming pockets are aligned as annular rows.

13. The surgical stapler of claim 9, wherein the first depth of all staple forming cups on a first row is equal to one another and the second depth of all staple forming cups in the first row is of variable depth.

14. The surgical stapler of claim 11, wherein the first and second staple forming cups are aligned at an angle with respect to the axis of the row of staple forming cups.

* * * * *